United States Patent [19]

Carlier et al.

[11] Patent Number: 5,135,931

[45] Date of Patent: Aug. 4, 1992

[54] PYRIDINYLPIPERAZINE DERIVATIVES

[75] Inventors: Patrick Carlier, Chatel-Guyon; Claude Poisson, Riom; André Monteil, Chatel-Guyon, all of France

[73] Assignee: Akzo N.V., Arnhem, Netherlands

[21] Appl. No.: 712,374

[22] Filed: Jun. 10, 1991

[30] Foreign Application Priority Data

Jun. 11, 1990 [EP] European Pat. Off. ......... 904015989

[51] Int. Cl.$^5$ ................. A61K 31/495; C07D 213/74; C07D 401/04
[52] U.S. Cl. .................................... 514/252; 544/360; 544/364
[58] Field of Search ................. 544/360, 364; 514/252

[56] References Cited

U.S. PATENT DOCUMENTS

| | | | |
|---|---|---|---|
| 3,488,352 | 1/1970 | Schipper et al. | 544/400 |
| 3,574,839 | 4/1971 | Schipper et al. | 544/400 |
| 3,705,899 | 12/1972 | Regnier et al. | 544/400 |
| 4,510,140 | 4/1985 | Nardi et al. | 544/360 |
| 4,882,432 | 11/1989 | Abou-Gharbia et al. | 544/360 |
| 4,971,969 | 11/1990 | Carlier et al. | 544/360 |
| 4,988,814 | 1/1991 | Abou-Gharbia et al. | 544/360 |
| 5,010,078 | 4/1991 | Abou-Gharbia et al. | 544/360 |
| 5,026,853 | 6/1991 | Van Daele et al. | 544/360 |

FOREIGN PATENT DOCUMENTS

| | | | |
|---|---|---|---|
| 750766 | 11/1970 | Belgium | 544/400 |
| 1961100 | 7/1970 | Fed. Rep. of Germany . | |
| 2024350 | 11/1970 | Fed. Rep. of Germany . | |
| 93884 | 7/1967 | France . | |
| 1570446 | 6/1969 | France . | |
| 142770 | 5/1990 | Japan | 544/360 |

OTHER PUBLICATIONS

Catto et al, J. Med. Chem. 1987, 30, pp. 13–19.
March, Adv. Org. Chem. 3rd Edition, pp. 370–371.

Primary Examiner—Cecilia Shen
Attorney, Agent, or Firm—Donna Bobrowicz; William M. Blackstone

[57] ABSTRACT

Disclosed are compounds displaying improved preferential serotonin-1A binding activity. The claimed compounds have the formula:

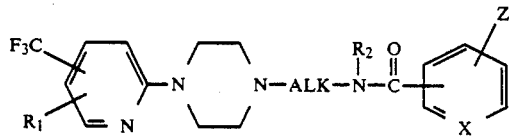

wherein
$R_1$ is selected from the group consisting of hydroxy, halogen, lower alkyl, lower alkoxy, and hydrogen;
$R_2$ is hydrogen or lower alkyl;
X is CH or a nitrogen atom;
ALK is a saturated, branched or unbranched, aliphatic hydrocarbon having from 1 to 7 carbon atoms; and
Z is selected from the group consisting of hydrogen, halogen, hydroxy, trifluoromethyl, or lower alkyl;
or a pharmaceutically acceptable salt thereof.

6 Claims, No Drawings

PYRIDINYLPIPERAZINE DERIVATIVES

FIELD

This invention relates to pyridinylpiperazine derivatives for use in treating depression.

STATE OF THE ART

French Patent No. 1,570,446 discloses compounds of the 2-amino- and 2-nitro-benzamide type. These compounds are disclosed as having relatively a low potency in central nervous system depressing and antipsychotic activities. The presence of an alkoxy group and of a nitrogen atom at the 2 position of the benzamide portion of the molecule is evidently important for this activity.

SUMMARY

Surprisingly it has been found that by removing the alkoxy group and the nitrogen atom of the benzamide moiety of the described molecule, or using other selected substituents, and by using a pyridinyl group instead of the phenyl group, the activity of the compound reverses from depressing the central nervous system to being anti-depressant. Moreover, the compounds of this invention are highly potent. The invention thus includes antidepressant compounds having a general structure of formula I:

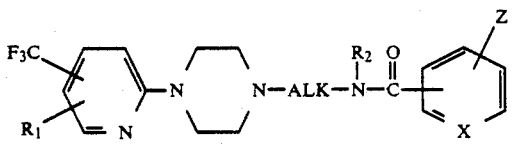

wherein
$R_1$ is selected from the group consisting of hydroxy, halogen, lower alkyl, lower alkoxy, and hydrogen;
$R_2$ is hydrogen or lower alkyl;
X is CH or a nitrogen atom;
ALK is a saturated, branched or unbranched, aliphatic hydrocarbon having from 1 to 7 carbon atoms; and
Z is selected from the group consisting of hydrogen, halogen, hydroxy, trifluoromethyl, or lower alkyl; or a pharmaceutically acceptable salt thereof.

The compounds display improved preferential 5-$HT_{1A}$ binding activity, with little or no dopamine antagonistic activity. The invention also includes processes for making the compounds and their salts. Once made, the compounds may be used in the manufacture of a medicament for the treatment and/or prevention of the occurrence or reoccurrence of depression. For example, the compounds are administered, on a regular basis, to a mammal, such as a human, believed to be depressed. A sufficient amount of compound is administered on a milligram per kilogram body mass basis, for a sufficient amount of time to combat the depression.

DESCRIPTION OF THE PREFERRED EMBODIMENTS

Preferred compositions display preferred binding activity to the 5-$HT_{1A}$ (serotonin 1A) receptors over the 5-$HT_{1B}$ (serotonin 1B) receptor. Preferably the pKi (binding constant) of the serotonin 1A receptors will exceed 7, and most preferably exceed 8. The pKi of the serotonin 1B receptor will therefore be less than the pKi of the serotonin 1A receptor for a particular compound.

Preferably, in a compound of formula I, ALK is an unbranched saturated aliphatic hydrocarbon having between 2 and 5 carbon atoms, and most preferably 2 carbon atoms, X is CH, $R_1$ and $R_2$ are hydrogen, and Z is hydrogen or halogen, and more preferably fluorine.

The trifluoromethyl group is preferably attached to position 4 or 6 of the pyridinyl ring. The most preferred compound is 4-fluoro-N-[2-[4-[6-(trifluoromethyl)-2-pyridinyl]-1-piperazinyl]ethyl]benzamide or a pharmaceutically acceptable salt thereof. ALK can be saturated or unsaturated. Examples are 1,2-ethanediyl, 1,3-propanediyl, 1,4-butanediyl, 1-methyl-1, 2-ethanediyl, 2,4-dimethyl-1,4-butanediyl, and 2-butene-1, 4-diyl. Preferred ALK groups are unbranched hydrocarbon groups with 2-5 carbon atoms. Most preferred is the 1,2-ethanediyl group.

For $R_2$, "lower alkyl" is preferably methyl. As used herein, the term lower alkyl means a branched or unbranched alkyl group having one to four carbon atoms, such as methyl, ethyl, propyl, butyl, or isopropyl.

The term lower alkoxy means an alkoxy group having an alkyl moiety which is the same as defined for "lower alkyl". Preferred lower alkoxy is the methoxy group.

The term halogen, used in the definition of formula I, means fluorine, chlorine, or bromine.

Once the structure of these compounds is known, methods of making the compounds will be known to those skilled in the art. However, as more thoroughly described in the Examples, methods of making the compounds generally involve alkylating the terminal primary amine group of a compound having the formula

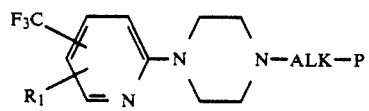

or derivatives thereof, wherein $R_1$, and ALK have the previously defined meanings, and P is $NHR_2$ (wherein $R_2$ has the previously given meaning) or Hal, wherein Hal is a halogen atom (e.g. chlorine, bromine, or iodine), with a substituted or unsubstituted benzoyl halide compound having the formula

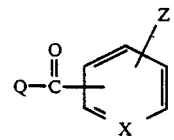

wherein Z and X have the previously defined meanings and Q is Hal when P is $NHR_2$, or $NHR_2$ when P is Hal.

The compounds of formula I may also be prepared by the condensation of a pyridine derivative having the formula

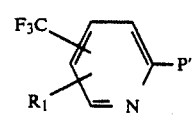

wherein $R_1$ has the previously given meaning and P' is Hal (as previously defined) or 1-piperazinyl, with a compound having formula

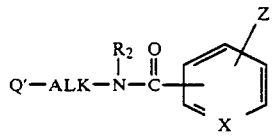

wherein R$_2$, ALK, X, and Z have the previously given meanings, and Q' is Hal when P' is 1-piperazinyl, or 1-piperazinyl when P' is Hal.

It is possible to convert the products obtained by one of the previously mentioned procedures into another product according to the invention. Using generally known methods it is, for instance, possible to convert aromatic substituents into other aromatic substituents. Alkoxy substituents may be treated with strong acids such as BBr$_3$, to give the hydroxy substituent. Hydroxy substituted compounds may be condensed with lower alcohols in acidic medium to give alkoxy derivatives. Compounds wherein R$_2$ is hydrogen may be alkylated, e.g. by a Leuckart-Wallach reaction, to afford compounds wherein R$_2$ is alkyl.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, H$_2$SO$_4$, H$_3$PO$_4$, acetic acid, propionic acid, glycolic acid, maleic acid, malonic acid, methanesulphonic acid, fumaric acid, succinic acid, tartaric acid, citric acid, benzoic acid, or ascorbic acid. Especially preferred are the hydrochloric and fumaric acid salts, although the free base itself may also be used.

Administration of the described compounds is useful in the prevention and treatment of depression. The dosage administered will generally be dependent upon the severity of depression to be treated, the type of patient involved, his age, health, weight, kind of concurrent treatment, if any, length and frequency of treatment and therapeutic ratio of the particular compound.

The dosage forms will be administered over varying durations. To treat depression, the compounds are administered to a patient for a length of time sufficient to alleviate the symptoms associated with the depression that the patient is suffering from. This time may vary, but periods of time exceeding two weeks are especially preferred. After the symptoms have alleviated, the compound may then be discontinued to determine whether it is still required by the particular patient.

To prevent the occurrence or reoccurrence of depression, and thus alleviate the need for treatment, the compounds are administered to a person believed to be susceptible to these disorders for so long as he or she is believed susceptible. Persons who may be susceptible to these disorders include those genetically predisposed, those undergoing drug withdrawals, those who have suffered a personal loss, etc. The length of such preventative administration of the compounds will of course vary, but again, periods of time exceeding two weeks are preferred. If the reason for the supposed susceptibility to depression has ceased to exist, the compound may then be discontinued.

Illustratively, dosage levels of the administered active ingredients can be between 0.1 mg and 10 mg per kg of body mass. In human therapy, daily doses of between 1 mg and 1000 mg, administered orally, will preferably be used. The pharmaceutical compositions containing the described compounds are preferably administered in unit dosage forms, such as tablets, capsules, pills, powders, granules, suppositories, sterile parenteral solutions or suspensions and non-parenteral solutions or suspensions, containing suitable quantities of an active ingredient or pharmaceutically acceptable salt of an active ingredient. For oral administration, either solid or fluid unit dosage forms can be prepared.

Methods and compositions for making such dosage forms are well-known to those skilled in the art. For example, methods and compositions for making tablets and pills, containing active ingredients, are described in the standard reference, Chase et al., *Remington's Pharmaceutical Sciences*, (16th ed., Mack Publishing Co., Easton, Pa., U.S.A., 1980).

The term "unit dosage form" as used herein generally refers to physically discrete units suitable as unitary dosages for humans and animals, each containing a predetermined quantity of active material calculated to produce the desired psychotropic effect.

The invention is further explained by reference to the following examples.

EXAMPLE I 4-fluoro-N-[2-[4-[6-(trifluoromethyl)-2-pyridinyl]-1-piperazinyl]ethyl]benzamide (E)-2-butenedioate (1:1) salt was made according to the following method.

a. 54.4 g of 2-chloro-6-trifluoromethyl pyridine are dissolved into a mixture of 350 ml of acetonitrile and 77.4 g of anhydrous piperazine. The mixture is filtered and washed with acetonitrile. The solvent is evaporated. The residue is taken up with dichloromethane and washed with water. The solution is dried over magnesium sulfate. The solvent is evaporated and the residue distilled, to obtain 56.4 g of 1-[6-(trifluoromethyl)-2-pyridinyl]piperazine (81.4% yield), having a boiling point of 103° C. at 0.05 mm Hg.

b. A mixture of 69.3 g of 1-[6-(trifluoromethyl)-2-pyridinyl]piperazine, and 129.6 g of N-(2-bromoethyl)phthalimide and 57.2 g of sodium carbonate is heated at reflux for 23 hours. The resulting precipitate is filtered off and the ethanol evaporated. The concentrate is dissolved in dichloromethane, washed with water, dried over magnesium sulfate, and evaporated. The resulting precipitate is recrystallized from isopropanol to give 39.5 g of 2-μ-[4-[6-(trifluoromethyl)-2-pyridinyl]-1-piperazinyl]ethyl]-1H-isoindole-1,3-dione (yield 33%).

c. A mixture of 39.5 g of the compound of 2-[2-[4-[6-(trifluoromethyl)-2-pyridinyl]-1-piperazinyl]ethyl]-1H-isoindole-1,3-dione and 7.3 g of hydrazine hydrate in 250 ml of ethanol is heated at reflux for 2 hours. After addition of 300 ml of 1 N HCl, the resulting mixture is heated at reflux for two hours. The resulting precipitate is filtered off, and the solution washed twice with diethyl ether (200 ml). The solution is basified with sodium hydrogen carbonate and extracted with dichloromethane. The extract is dried on magnesium sulfate and the solvent evaporated to yield 24.7 g of 4-[6-[(trifluoromethyl)-2-pyridinyl]piperazine-1-ethanamine (yield 93%).

d. A cold mixture (0° C.) of 20 g of 4-[6-[(trifluoromethyl)-2-pyridinyl]piperazine-1-ethanamine and 12.1 g of triethylamine in 200 ml of toluene is added dropwise to 13 g of 4-fluorobenzoyl chloride. The mixture is stirred for 1 hour at room temperature. The resulting precipitate is filtered and washed with dichloromethane. The resulting solution is evaporated and the concentrate dissolved in dichloromethane, washed successively with diluted sodium hydrogen carbonate and water. The organic phase is dried on magnesium sulfate, and evaporated to yield the crude base which is recrystallized from 2-methyl-1-propanol to give 14.1 g of purified base. The fumarate salt is prepared by adding 2.4 g of fumaric acid in absolute ethanol to the base. The resulting compound is recrystallized twice from absolute ethanol and twice from isopropanol, thus yielding 14.8 g (yield 40%) of 4-fluoro-N-[2-[4-(6-trifluoromethyl-2-pyridinyl) -1-piperazinyl]ethyl]benzamine (E)-2-butenedioate (1:1). mp 152° C.

EXAMPLE II

N-[2-[4-[6-(trifluoromethyl)-2-pyridinyl]-1-piperazinyl]ethyl]benzamide (E)-2-butenedioate (1:1) salt was made according to a method similar to that described for Example I, but using 9.8 g of 4-[6-(trifluoromethyl) -2-pyridinyl]-1-piperazine and 5.9 g of triethylamine in 100 ml toluene after addition of 5.4 g of benzoyl chloride, thus obtaining 4.4 g of base, the fumarate salt of which has a melting point of 175° C.

EXAMPLE III 4-fluoro-N-[2-[4-[4-(trifluoromethyl) -2-pyridinyl]-1-piperazinyl]ethyl]benzamide (E)-2-butenedioate (1:1) salt was made according to a method similar to that described for Example Id, but using 10.1 g of 4-[4-(trifluoromethyl)-2-pyridinyl]piperazine-1-ethanamine, 6.4 g of triethylamine, 100 ml of toluene, and 6.5 g of 4-fluorobenzoyl chloride, thus obtaining 12.2 g of base which can be converted into the monofumarate as previously described giving 5.4 g of 4-fluoro-N-[2-[4-[4-(trifluoromethyl)-2-pyridinyl]-1-piperazinyl]ethyl]-benzamide, which has a melting point of 159° C.

EXAMPLE IV 4-fluoro-N-[4-[4-[6-(trifluoromethyl) -2-pyridinyl]-1-piperazinyl]butyl]benzamide (E)-2-butenedioate (2:1) salt was made according to the following procedure:

a. Using the same method as described in Example Ic, but with 64.8 g of 2-[4-[4-(6-trifluoromethyl-2-pyridinyl)-1-piperazinyl]butyl]-1H-isoindole-1,3-dione, thus obtaining 44 g of 4-[6-trifluoromethyl) -2-pyridinyl]piperazine-1-butanamine (yield 93%).

b. Using the same method as in Example Id, starting with 15.1 g of Example IVa, thus obtaining 11.4 g of purified base. The hemifumarate is prepared, as usual, in absolute ethanol, yielding 8.2 g (39%) of 4-fluoro-N-[4-[4-[6-(trifluoromethyl)-2-pyridinyl]-1-piperazinyl]-butyl]benzamide (E)-2-butenedioate (2:1) salt. mp 186.6° C.

EXAMPLE V

N-[4-[4-[6-(trifluoromethyl)-2-pyridinyl]-1-piperazinyl]butyl]benzamide (E)-2-butenedioate (2:1) salt was made according to a method similar to that described for Example IV, but using benzoyl chloride, after which the hemifumarate salt was obtained having a melting point of 206° C.

EXAMPLE VI

N-[2-[4-[6-(trifluoromethyl)-2-pyridinyl]]-1-piperazinyl]ethyl]pyridinecarboxamide was made according to a method similar to that described for Example I, but using nicotinoyl chloride instead of 4-fluorobenzoyl chloride in Example Ic. mp 114° C.

EXAMPLE VII 4-fluoro-N-[2-[4-(6-(trifluoromethyl)-2-pyridinyl)-1-piperazinyl]ethyl]-N-methylbenzamide was prepared, the fumarate salt of which had a melting point of 144° C.

EXAMPLE VIII 4-fluoro-N-[3-[4-(6-(trifluoromethyl)-2-pyridinyl)-1-piperazinyl]propyl]-N-methylbenzamide was prepared, the fumarate salt of which had a melting point of 176° C.

EXAMPLE IX

The various compounds of Examples I–VIII were analyzed for serotonin binding activity. Average test results are given in the following table:

| Example | pKi 5-HT$_{1A}$ | pKi 5-HT$_{1B}$ |
| --- | --- | --- |
| I | 8.8 | <5 |
| II | 9.0 | 5 |
| III | 7.7 | 5 |
| IV | 8.1 | 6.3 |
| V | 8.2 | 6 |
| VI | 7.3 | 5.3 |
| VII | 7.5 | <5 |
| VIII | 7.2 | <5 |

We claim:
1. A compound of the formula:

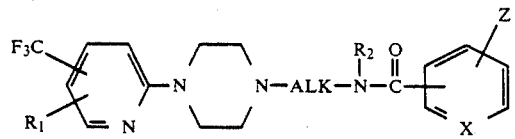

wherein
$R_1$ is selected from the group consisting of hydroxy, halogen, lower alkyl wherein said lower alkyl is a branched or unbranched alkyl having one to four carbon atoms, lower alkoxy having an alkyl moiety that is a branched or unbranched and has one to four carbon atoms, and hydrogen;
$R_2$ is hydrogen or said lower alkyl;
X is CH or a nitrogen atom;
ALK is a saturated, branched or unbranched, aliphatic hydrocarbon having from 1 to 7 carbon atoms; and
Z is selected from the group consisting of hydrogen, halogen, hydroxy, trifluoromethyl, or said lower alkyl;
or a pharmaceutically acceptable salt thereof.

2. The compound of claim 1, wherein ALK has 2 to 5 carbon atoms, X is CH, Z is hydrogen or halogen, and $R_1$ and $R_2$ are hydrogen; or a pharmaceutically acceptable salt thereof.

3. The compound of claim 1, wherein ALK has 2 carbon atoms, X is CH, Z is halogen, $R_1$ and $R_2$ are hydrogen; or a pharmaceutically acceptable salt thereof.

4. The compound of claim 1, wherein said compound is 4-fluoro-N-[2-[4-[6-(trifluoromethyl)-2-pyridinyl]-1-piperazinyl ]ethyl]benzamide or a pharmaceutically acceptable salt thereof.

5. A pharmaceutical preparation comprising a pharmaceutically effective amount to treat or prevent depression of the compound of claim 1 and pharmaceutically acceptable auxiliaries.

6. A method of treating or preventing depression in a mammal comprising: administering to said mammal, on a regular schedule for a period of time, an antidepressant effective amount of the compound of claim 1 to treat the depression or prevent the occurrence of said depression.

* * * * *